United States Patent

Blue et al.

[11] Patent Number: 5,935,826
[45] Date of Patent: Aug. 10, 1999

[54] GLUCOAMYLASE CONVERTED STARCH DERIVATIVES AND THEIR USE AS EMULSIFYING AND ENCAPSULATING AGENTS

[75] Inventors: Emily Keller Blue, Indianapolis, Ind.; Chung-Wai Chiu, Westfield, N.J.; Zahera Hussain, Hyde Park, N.Y.; Himanshu Shah, Branchburg; Paul Trubiano, Somerville, both of N.J.

[73] Assignee: National Starch and Chemical Investment Holding Corporation, Wilmington, Del.

[21] Appl. No.: 08/962,285

[22] Filed: Oct. 31, 1997

[51] Int. Cl.$^6$ ..................................................... C12P 19/20
[52] U.S. Cl. ............................... 435/96; 435/98; 435/99; 536/102; 536/110; 536/107; 510/471; 510/474
[58] Field of Search .................................. 435/96, 99, 98; 536/102, 110, 107; 510/474, 471

[56] References Cited

U.S. PATENT DOCUMENTS

| | | | |
|---|---|---|---|
| 2,613,206 | 10/1952 | Caldwell | 260/233.5 |
| 2,661,349 | 12/1953 | Caldwell et al. | 260/224 |
| 3,971,852 | 7/1976 | Brenner et al. | 426/103 |
| 4,689,235 | 8/1987 | Barnes et al. | 426/89 |
| 4,977,252 | 12/1990 | Chiu | 536/102 |
| 5,087,461 | 2/1992 | Levine et al. | 426/96 |
| 5,185,176 | 2/1993 | Chiu | 426/651 |

FOREIGN PATENT DOCUMENTS 0 550 067   7/1993   European Pat. Off. .......... A23L 1/22

OTHER PUBLICATIONS

*Enzyme Nomenclature*, Academic Press, Inc. New York, 1984, pp. 308–309.

*Primary Examiner*—Francisco Prats
*Attorney, Agent, or Firm*—Karen G. Kaiser

[57] ABSTRACT

The present invention relates to modified starches which are prepared by enzymatic hydrolysis of a starch molecule using glucoamylase after the preparation of a starch derivative containing a hydrophobic group or both a hydrophobic and a hydrophilic group, particularly octenyl succinic anhydride starch hydrolyzed by glucoamylase. Such modified starches are useful as emulsifying and/or encapsulating agents, particularly in systems where high load and retention of the active ingredient, low surface oil exposure, and excellent oxidation resistance is desired.

27 Claims, No Drawings

GLUCOAMYLASE CONVERTED STARCH DERIVATIVES AND THEIR USE AS EMULSIFYING AND ENCAPSULATING AGENTS

BACKGROUND OF THE INVENTION

The present invention relates to a modified starch which is prepared by hydrolysis of a starch molecule using glucoamylase after the preparation of a starch derivative containing a hydrophobic group or both a hydrophobic and a hydrophilic group. Such modified starch is useful as an emulsifying agent or as an encapsulating agent, particularly in systems where high load and retention of the active ingredient, low surface oil exposure, and excellent oxidation resistance is desired.

U.S. Pat. Nos. 4,977,252 and 5,185,176 issued to Chiu disclose starch derivatives containing a hydrophobic or both a hydrophobic and a hydrophilic group which have been enzymatically degraded by exo-enzymes which exhibit selectivity in cleaving the 1,4-linkages and leaving the 1,6-linkages intact. These modified starches are useful as emulsifiers.

A variety of chemical compositions are conventionally used as encapsulating agents in, inter alia, the food, cosmetic, paint, pharmaceutical, personal care, and polymer industries. Typical compositions which conventionally function as encapsulating agents include gum arabic, dextrins, low viscosity modified starches, arabinogalactan, gum acacia, casein, gelatin, carboxymethyl cellulose, and tragacanth, karaya, sodium alginate, tannin, and celluloses.

These typical compositions however do not consistently provide high active agent loading and retention, low surface oil and excellent oxidation resistance. In general, powders prepared with conventional encapsulating agents do not contain a high level of active agents. When loaded with oil levels of higher than 15–20%, such conventional encapsulated powders lose a considerable amount of the oil during the drying process, have much of the oil exposed on the surface of the powder, and/or generally have poor oxidation resistance.

U.S. Pat. No. 3,971,852 issued to Brenner, et al. discloses a method for encapsulating oils in particles of a solid water-sensitive, preferably water-soluble, protective matrix that isolates the oils until they are released for use by exposure of the particles to moisture. The matrix-forming encapsulation materials include mixtures of polysaccharides and polyhydroxy compounds that can form aqueous emulsions with the oil. Although the patent claims efficient encapsulation of up to 80% by volume and surface oil not substantially above 5%, with a relatively high loading, the known process fails to provide efficient encapsulation oil recovery with excessive oil loss during drying and extractable oils as high as 10-24% when the encapsulated oil content exceeds 60% by weight. Furthermore, it has not been shown that these matrices provide good oxidation resistance.

U.S. Pat. No. 5,087,461 issued to Levine, et al. discloses a spray dried composition encapsulated in an extruded glassy matrix composed of a chemically modified starch having a dextrose equivalent no greater than 2, a maltodextrin, a corn syrup solid or polydextrose, and a mono- or di-saccharide. However, these encapsulated products are unable to achieve high loading and are susceptible to oxidation.

EP Patent Application No. 550 067 A1 discloses a method for encapsulating oils in a water-sensitive cellular solid matrix by drying an aqueous emulsion containing the oil to be encapsulated, a non-crosslinked lipophilically modified starch that undergoes crosslinking during drying, and a polyhydroxy compound that forms with the polysaccharide material a continuous aqueous phase in which the oil is dispersible as a discontinuous phase. This method of encapsulation is unacceptable for foods and pharmaceuticals and requires the incorporation of a silicone-based material which is difficult to process using conventional methods. Furthermore, it has not been shown that these matrices provide good oxidation resistance.

However, none of the encapsulating agents known in the art provide a high load of at least 40% while maintaining a retention of at least 90% of the active ingredient with less than 3% surface oil exposure, and excellent oxidation resistance for a wide variety of encapsulating agents. Surprisingly, it has now been discovered that the present invention which uses a modified starch, prepared by enzymatically converting a starch using glucoamylase after the preparation of a starch derivative containing a hydrophobic group or a hydrophobic and a hydrophilic group, as an encapsulating agent, may consistently allow for such high load and retention of a variety of active ingredients and low oil exposure while providing excellent oxidation resistance. Further, such glucoamylase degraded starch derivatives are excellent emulsifiers.

SUMMARY OF THE INVENTION

The present invention is directed to a modified starch which is prepared by enzymatic hydrolysis of a starch molecule using glucoamylase after the preparation of a starch derivative containing a hydrophobic group or both a hydrophobic and a hydrophilic group. Such modified starch is useful as an emulsifying agent and as an encapsulating agent, particularly in systems where high load and retention of the active ingredient, low surface oil exposure, and excellent oxidation resistance is desired.

An object of the present invention is to provide a glucoamylase converted, starch derivative containing a hydrophobic group or a hydrophobic and a hydrophilic group and a method of producing such starch.

Another object of the present invention is to provide a glucoamylase hydrolyzed, hydrophobically derivatized starch.

Still another object of the present invention is to provide a glucoamylase hydrolyzed, alkenyl succinic starch.

Yet another object of the present invention is to provide a glucoamylase converted, starch derivative containing a hydrophobic group or a hydrophobic and a hydrophilic and a method of producing such starch.

Still yet another object of the present invention is to provide products containing a glucoamylase converted, starch derivative containing a hydrophobic group or a hydrophobic and a hydrophilic group as an emulsifier or as an encapsulating agent and a method of preparing such products.

A further object of the present invention is to provide products containing a glucoamylase hydrolyzed, hydrophobically derivatized starch as an emulsifying or as an encapsulating agent.

A still further object of the present invention is to provide products containing a or glucoamylase hydrolyzed, alkenyl succinic starch as an emulsifying or as an encapsulating agent.

These and other objects of the present invention will become apparent to one skilled in the art from the following detailed description and examples below.

DETAILED DESCRIPTION OF THE INVENTION

The present invention is directed to a modified starch which is prepared by enzymatic hydrolysis of a starch molecule using glucoamylase after the preparation of a starch derivative containing a hydrophobic group or both a hydrophobic and a hydrophilic group. Such modified starch is useful as an emulsifying and/or as an encapsulating agent. In particular, these starches are useful as encapsulating agents in systems where high load and retention of the active ingredient, low surface oil exposure, and excellent oxidation resistance is desired. Further, such encapsulating agents can be processed at high solids during the encapsulation process.

All starches and flours are suitable for use herein and may be derived from any native source. A native starch or flour, as used herein, is one as it is found in nature, including those developed by plant breeding, and bioengineered starches. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 45% by weight amylose. In particular, corn, waxy maize, tapioca, potato, and rice are useful in the instant invention.

Also included as useful base starch materials are the conversion products derived from any of the above starches including fluidity or thin-boiling starches prepared by oxidation, a-amylase conversion, mild acid hydrolysis or heat dextrinization, and derivatized starch such as ethers and esters.

A particularly useful starch base is a gelatinized starch, that is a precooked, non-granular starch, and also may be a fluidity starch converted by mild acid degradation or heat dextrinization methods that are well known in the art. For example, see Rutenberg, "Starch and Its Modifications," *Handbook of Water-Soluble Gums and Resins*, Davidson, Editor, McGraw-Hill, Inc., New York, N.Y., 1980, pp.22–36. A combination of one or more of these conversion techniques may be used. The conversion is typically carried out before treatment with a hydrophobic or a hydrophobic/hydrophilic reagent and before the enzyme treatment. If desired, the starch base may be converted by treatment with an (x-amylase enzyme to produce a fluidity starch in the manner disclosed in U.S. Pat. No. 4,035,235. Where a high viscosity system is desired, it is not necessary to convert the base starch.

The starch may be derivatized by treatment with any reagent or combination of reagents which contributes emulsifying and/or encapsulating properties to the starch. The reagent must contain a hydrophobic moiety and may contain a hydrophilic moiety. The hydrophobic moiety should be an alkyl or an alkenyl group which contains at least five carbon atoms or an aralkyl or aralkenyl group which contains at least six carbon atoms, particularly up to about twenty-four carbon atoms. The hydrophilic moiety may be contributed by the reagent or the starch's own hydroxyl groups may serve as the hydrophilic moiety and the reagent may contribute only the hydrophobic moiety.

Any process for derivatizing starch which yields the desired blend of hydrophobic or hydrophobic and hydrophilic functions on the starch molecule and thereby yields stable encapsulation properties may be used to prepare the modified starch of the present invention. Suitable derivatives and methods for producing them are known in the art and disclosed in U.S. Pat. No. 4,626,288 which is incorporated herein by reference. In a particularly useful embodiment, the starch is derivatized by reaction with an alkenyl cyclic dicarboxylic acid anhydride by the method disclosed in U.S. Pat. Nos. 2,613,206 and 2,661,349, incorporated herein by reference, or propylene oxide, more particularly by reaction with octenylsuccinic anhydride.

Where a low viscosity is desirable, a particularly useful embodiment is an octenyl succinic half ester derivative of an amylopectin containing starch, such as waxy maize, which has been converted to a water fluidity (WF) of up to about 60. Water fluidity is an empirical test of viscosity measured on a scale of 0–90 wherein fluidity is the reciprocal of viscosity. Water fluidity of starches is typically measured using a Thomas Rotational Shear-type Viscometer (commercially available from Arthur A. Thomas CO., Philadelphia, Pa.), standardized at 30° C. with a standard oil having a viscosity of 24.73 cps, which oil requires 23.12±0.05 sec for 100 revolutions. Accurate and reproducible measurements of water fluidity are obtained by determining the time which elapses for 100 revolutions at different solids levels depending on the starch's degree of conversion: as conversion increases, the viscosity decreases. In a particularly useful embodiment, the converted starch is treated with at from about 0.1% to about 3.0% for food products and at least about 0.1% for other products, of the octenyl succinic anhydride. In the alternative, a hydroxypropyl octenyl succinic derivative may be used.

For other products, any degree of substitution or level of conversion that results in the desired viscosity and encapsulation properties may be employed. For example, U.S. Pat. No. 4,035,235 disclosed a suitable embodiment comprising a method for producing a hydrophobic derivative of starch to be used as an alternative to gum arabic in encapsulating water insoluble substances, such as volatile flavoring oils and perfumes.

After derivatizing the starch, it is further enzymatically hydrolyzed by glucoamylase. The enzymatic hydrolysis of the starch base is carried out using techniques known in the art. The amount of enzyme used is dependent upon the enzyme source and activity, base material used, and the amount of hydrolysis desired. Typically, the enzyme is used in an amount of from about 0.01 to about 1.0%, particularly from about 0.01 to 0.3%, by weight of the starch.

The optimum parameters for enzyme activity will vary depending upon the enzyme used. The rate of enzyme degradation depends upon factors known in the art, including the enzyme concentration, substrate concentration, pH, temperature, the presence or absence of inhibitors, and the degree and type of modification. These parameters may be adjusted to optimize the digestion rate of the starch base.

The starch may be gelatinized before glucoamylase hydrolysis. The gelatinization process unfolds the starch molecules from the granular structure, thereby permitting the enzyme to more easily and uniformly degrade the starch molecules. However, as glucoamylase can hydrolyze granular starch, gelatinization is not necessary.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

The enzyme reaction is continued until a dextrose equivalent of at least about 20 and up to about 80, particularly about 30 to about 50, has been achieved, or until the desired end point (i.e., sufficient degradation to provide the desired functionality for the particular application) has been reached. The end point may be determined by a change in viscosity, by reducing sugar content (such as measured by dextrose equivalents), or by any other method known in the art for measuring the level of enzyme degradation of the starch molecule. In general, the enzyme reaction will take from about 0.1 to about 24 hours, particularly about 0.5 to about 4 hours. The time of the reaction is dependent upon the type of starch used, the amount of enzyme used, and the reaction parameters of solids percent, pH, and temperature.

The enzyme degradation is then terminated by any technique known in the art such as acid or base deactivation, heat deactivation, ion exchange, and solvent extraction. For example, acid deactivation may be accomplished by adjusting the pH to lower than 2.0 for at least 30 minutes or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The resultant solution is typically adjusted to the desired pH according to its intended end use. In general, the pH is adjusted to from about 5.0 to about 7.5, particularly from about 6.0 to about 7.0, using techniques known in the art. The modified starch is then typically dried using methods known in the art, particularly spray drying. However, the modified starch may also be used as a liquid concentrate.

The resulting starch is characterized by a relatively low viscosity, moderately high dextrose equivalent, neutral taste, and by its unique functionality as an encapsulating agent.

The viscosity of the resultant starch should be less than about 30 seconds, particularly from about 8 to about 25 seconds, more particularly from about 8 to about 15 seconds as measured by the funnel method. Viscosity is an important parameter in contributing to efficient encapsulation.

To measure the viscosity of the starch is measured by the funnel method. The starch dispersion to be tested is adjusted to 19% or 25% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder is then inverted over the funnel so that the contents draw (flow) into the funnel while the sample is running. Using a timer, the time required for the 100 ml sample to flow through the apex of the funnel is recorded.

The glass portion of the funnel is a standard 580, thickwall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip with is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

The resultant starch should have a dextrose equivalent of at least about 20 and up to about 80, particularly from about 30 to about 50. Dextrose equivalent (DE) is defined as the reducing power of the hydrolyzate. Each starch molecule has one reducing end: therefore DE is inversely related to molecular weight. The DE of anhydrous D-glucose is defined as 100 and the DE of unhydrolyzed starch is virtually zero.

The resultant starch should have a relatively high percent of sugars, at least about 20 and up to about 80% sugar, particularly from about 30 to about 40% glucose, more particularly from about 30 to about 35% glucose.

The active agent may be any substance which will not react with the starch system, including but not limited to oils, fats, flavors, colors, fragrances, vitamins, and pharmaceuticals. In particular, the modified starch of the present invention is useful for emulsifying or encapsulating oil-based active agents such as flavor oils and vitamins. These oils may be volatile or non-volatile and are generally characterized by being water immiscible but dispersible (emulsifiable) in water in the presence of an encapsulating agent.

The resultant starches, when used as emulsifying agents, have the advantages of improved shelf stability and resistance to oiling, gelling, and ringing during storage.

The resultant starches, when used as encapsulating agents, have the advantages of achieving and maintaining consistently high load levels, low oil exposure, and excellent oxidation resistance.

The active agents may be encapsulated using the modified starches of the present invention and techniques known in the art, including but not limited to spray drying, extrusion, spray chilling, and fluid bed coating. For example, the starch may be dispersed in water, the active agent may be added and emulsified, and the emulsion may then be spray dried to form the encapsulated product.

The encapsulated product prepared with the present encapsulating agents consistently achieve and maintain a relatively high load level of the active agent. The load level of the active agent realized may be greater than 40%, particularly greater than 50%, more particularly greater than 60%, by weight of the encapsulating agent. The level of active agent retained may be determined by methods known in the art such as by hydro-distillation in the case of flavor oils or by solvent extraction alone in the case of vitamins.

A high load level of active agent is desirable to reduce the cost of producing the final product as encapsulating agents are often expensive. Further, some encapsulating agents may contribute adverse or undesirable properties to the final system and it is thus desirable to reduce the amount of encapsulating agent used.

It is important not only to achieve a high load of active agent, but also to maintain it so as to enable a longer shelf life. Many active agents are volatile and/or labile, particularly flavors and fragrances. When the active agents are not encapsulated, they may be lost, producing undesirable variations in taste and aroma of the final products as perceived by the consumer. In addition, losses of such components increase the cost of the final products since it is necessary to increase the amount of the volatile/labile component to compensate for the losses which occur, and many are expensive.

In the case of oil as an active agent, the present encapsulating agents also retain the oil so as to provide a low surface oil. This is particularly true when glucoamylase is used to enzymatically hydrolyze the starch. The surface oil may be measured by methods known in the art such as by washing the encapsulated powder with a suitable solvent. Reduction of surface oil is important as increased surface oil indicates that the load of the active agent is not being maintained and inefficiency of encapsulation. Thus, reduction of surface oil results in a longer shelf life.

The present encapsulating agents also provide a relatively high level of oxidation resistance, thereby prolonging storage stability of the encapsulated product and shelf life of the final product. Oxidation resistance may be measured by methods known in the art. For example, oxidation resistance of encapsulating agents containing citrus oil may be determined by using gas chromatography (GC) to measure the amount of oxidization products of limonene, such as carvone, carviol, and limonene oxide, present in the oil extracted from powders aged at 50° C. for two weeks: less than about 0.8% carvone typically indicates acceptable levels of oxidation. Oxidation resistance is important not only for flavor considerations of the oil, but also to maintain the activity of various vitamins. To further increase oxidation resistance, an anti-oxidant may be added to the oil.

The encapsulated product is effective when stored as a powder and spontaneously releases the active agent upon exposure to moisture. The resultant encapsulated product may be used at any level desired in food products, the amount being dependent upon the amount of active agent to be incorporated. In general, the starch will be used in an amount of from about 0.01 to about 10%, particularly from about 0.1 to about 5% by weight of the food product.

The resultant starch can be used in various food products including, but not limited to, cereals; powdered drink mixes; instant coffees and teas; powdered sauce and gravy mixes; instant soups; cereals; powdered dressings; bakery products; flavors; fragrances; colorants; and other dry food products. Upon preparation of these powdered and instant products, the moisture triggers the release mechanism, providing the active agent to the consumer.

The resultant starch may also be used in a variety of pharmaceuticals including vitamins; personal care products including antiperspirants, deodorants, soaps, fragrances, and cosmetics; hair care products, such as hair sprays, mousses, shampoos, cream rinses, and gels; paper products such as diapers, sanitary napkins, paper towels, tissues, toilet tissues; animal care products such as kitty litter; and household products such as carpet cleaners, and air fresheners.

The following examples are presented to further illustrate and explain the present invention and should not be taken as limiting in any regard.

EXAMPLES

The following examples are presented to further illustrate and explain the present invention and should not be taken as limiting in any regard. The following analytical tests were used to measure various parameters in the examples.

Determination of Dextrose Equivalents (DE)

The dextrose equivalent of starch may be determined by using the Reducing Sugars test described in Food Chemicals Codex, 4th ed., Jul. 1, 1996. Section 5, General Tests and Assays, Appendix X: Carbohydrates (Starches, Sugars, and Related Substances) or Standard Analytical Method #E-26 for Dextrose Equivalent from the Corn Refiners Association.

Oxidation Resistance Analysis

Twenty (20) grams of the modified starch powder loosely filled, were placed in a one liter jar with a powder to air ratio of 1:25. The jar was capped tightly with Teflon. The sample was placed in a 50° C. oven for two weeks.

The oil was then distilled using hydro-distillation. The distilled oil was then analyzed using gas chromatography for fresh (limonene) and oxidized (carvone) components.

Surface Oil Analysis

The unencapsulated oil present on the surface of the particle is repeatedly extracted using organic solvents, such as pentane, to remove all the surface oil and the extracted oil is quantitatively determined using gas chromatography techniques known in the art.

Oil Retention (Loading) Analysis

To determine the oil retention of the encapsulated product, 15 grams of the spray dried, encapsulated oil and 150 ml distilled water are mixed to reconstituted the emulsion. The emulsion is heated to reflux and held for four hours. The mixture is then cooled and the separated oil is removed and weighed.

$$\% \text{ Retention} = \frac{\text{volume of oil extracted} \times \text{specific gravity of oil}}{\text{theoretical oil weight}} \times 100$$

Example 1

Preparation of the Derivatized Starch 500 grams of waxy maize starch were slurried in 750 ml water. The pH was adjusted to 7.5 using 3% sodium hydroxide. 15 grams of octenylsuccinic anhydride (OSA) were added in one-third increments every thirty minutes while maintaining the pH at 7.5 using 3% sodium hydroxide with constant agitation. The starch was then filtered out and washed with 750 ml water. The starch was then reslurried in 500 ml water and the pH adjusted to 5.5 with 3:1 hydrochloric acid. The starch was then filtered, washed with 750 ml water, and air dried to produce an OSA starch.

Example 2

Preparation of the Modified Starch 100 grams of the OSA starch of Example 1 were slurried in 300 ml water and the pH adjusted to 5.5 using dilute hydrochloric acid. The slurry was gelatinized by jet cooking in a C1-339 jet cooker, commercially available from National Starch and Chemical Company, at 300° F., at a chamber pressure of 55 psi, and a slurry rate of 6 ml/min with the steam valve open at 75% capacity.

The temperature of the starch solution was then decreased to 55° C. 0.05% glucoamylase (AMG 200 L, commercially available from Novo Nordisk) based on the weight of the starch was added and the reaction was allowed to proceed at 55° C. with constant mixing for approximately 2.5 hours until a dextrose equivalent of 36 and a viscosity of 17 sec at 25% solids and 22° C. using the funnel method. The enzyme was then deactivated by heating the dispersion to 90° C. and maintaining the elevated temperature for 30 minutes. The dispersion was then cooled to room temperature and spray

Example 3
Encapsulation of Orange Oil with 40% Load 240 grams of the modified starch prepared in Example 2 was dispersed in 600 ml water in a high dispersion mill. The temperature was raised to 60° C. until the starch dissolution appeared complete and then was lowered to 40° C. 160 g of a single pressed orange oil commercially available from Givaudan-Roure was added and emulsified at high speed for approximately three minutes. The viscosity of the emulsion as determined using a Brookfield Viscometer Model 1+ using a small sample adaptor with spindle #18 is 85 cps at 40° C. The emulsion was sprayed dried to a powder.

The resultant encapsulated orange oil retained 38% oil based on the weight of the product, a 95% encapsulation of the oil used in the system; the surface oil (extractable oil) was 0.3%; the oxidation was found to be at acceptable levels after aging, 0.8% Carvone; and the moisture of the product was 1.9% as determined by the Karl-Fischer Method.

Example 4
Preparation of an Orange Drink Mix

| Ingredient | Amount (grams) |
| --- | --- |
| Example 3 encapsulated oil | 2.18 |
| Sugar | 95.58 |
| Citric Acid | 1.74 |
| FD&C Yellow #15 | 0.03 |
| FD&C Yellow #6 | 0.03 |
| Benzoic Acid | 0.44 |

The ingredients were dry blended to prepare a powdered orange drink mix. 11.51 grams of the mix were reconstituted with 88.5 ml water to produce a clean-tasting orange drink which was free from oxidized flavors.

Example 5
Encapsulation of Vitamin E 165 grams of the starch of example 2 were dispersed in 670 grams water in a high dispersion mill. The temperature was raised to 60° C. until the starch dissolution appeared complete and then was lowered to 40° C. 165 g of Vitamin E was added and emulsified at high speed for approximately three minutes. The emulsion was spray dried to a powder which contained 50% of 1000 IU Vitamin E.

Example 6
Use of the Modified Starch in a Pharmaceutical

| Ingredient | Amount (mg) |
| --- | --- |
| Example 5 encapsulated vitamin E | 800 |
| Magnesium Stearate | 5 |
| Tricalcium Phosphate | 5 |
| Microcrystalline cellulose | 190 |

Dry blend the ingredients and press into one gram tablets using a tablet press.

Example 7
Analysis of Encapsulation

A variety of glucoamylase degraded OSA starches were prepared using the method of Example 2 with the exception that hydrolysis was allowed to proceed to different degrees. The modified starches were used to encapsulate orange oil as in Example 3. The results of the encapsulation as reported below.

| | | Viscosity at 22° C. (sec) | | % Retention | | | |
| --- | --- | --- | --- | --- | --- | --- | --- |
| Enzyme | DE | 19% solids | 25% solids | Time = 0 | Time = 2 weeks at 50° C. | % Surface Oil | % Carvone |
| Gluco-amylase | 19.7 | — | — | 84.21 | 73.68 | 3.87 | 2.10 |
| Gluco-amylase | 30.3 | 10.7 | 19.8 | 86.61 | 78.95 | 1.31 | 1.12 |
| Gluco-amylase | 37.7 | 9.7 | 15.3 | 98.31 | 95.51 | 0.08 | 0.36 |
| Gluco-amylase | 48.3 | 7.7 | 9.5 | 91.62 | 89.47 | 0.19 | 0.58 |
| Gluco-amylase | 48.3 | 7.7 | 9.5 | 91.62 | 89.24 | 0.05 | .029 |
| Gluco-amylase | 30 | — | — | 98.20 | 81.24 | 1.94 | 1.06 |
| Gluco-amylase | 45 | — | — | 91.60 | 91.20 | 0.05 | 0.52 |

Example 8
Comparison with other encapsulating starches

Starch example 8a is a 50:50 blend of corn syrup solids and cold water soluble, acid degraded, OSA starch in which the starch is prepared by acid hydrolyzing the OSA starch of Example 1 to a water fluidity of about 65 and then spray drying.

Example 8b is the OSA starch of example 1.

The modified starches were used to encapsulate orange oil as in Example 3. The results of the encapsulation as reported below.

| | | | % Retention | | |
| --- | --- | --- | --- | --- | --- |
| Example | DE | Time = 0 | Time = 2 weeks at 50° C. | % Surface Oil | % Carvone |
| 8a | 23 | 84.20 | 74.40 | 4.54 | 1.03 |
| 8b | 0 | 56.0 | — | 12.0 | — |

No stability test was run on example 8b due to the poor retention. A comparison of the above results with those of example 7 shows the superior retention, and decreased surface oil and oxidation of the present starches.

Example 9
Preparation of an Antiperspirant

| Ingredient | Amount (grams) |
| --- | --- |
| Encapsulated fragrance | 1.00 |
| Dow Corning Fluid 344 | 49.0 |
| Cyclochem EDGS | 1.00 |
| Arlacel 165 | 1.00 |
| Promyristyl PM3 | 5.00 |
| Crodacol S-95NF | 17.00 |
| Rezal 36 GP Suf | 20.00 |
| DRY-FLO ® PC Starch | 6.00 |

The encapsulated fragrance is prepared by the methodology of Example 3, substituting the fragrance for the orange oil. Dow Corning Fluid 344 is cyclomethicone commercially available from Dow Corning.

Cyclochem EDGS is glycol distearate commercially available from Alcolac.

Arlacel 165 is glyceryl stearate and PEG 100 stearate commercially available from ICI.

Promyristyl PM3 is PPG-3 myristyl ether commercially available from Croda.

Crodacol S-95NF is stearyl alcohol commercially available from Croda.

Rezal 36 GP Suf is aluminum zirconium tetrachlorohydrex glycine commercially available from Reheis.

DRY-FLO® PC starch, a modified food starch used as a dusting and lubricating agent, is commercially available from National Starch and Chemical Company.

The Dow Corning Fluid 344, Cyclochem EDGS, Arlacel 165, and Promyristyl PM3 are mixed and heated to 65° C. The Crodacol S-95NF is mixed in thoroughly.

The Rezal 36 GP Suf is added and mixed for ten minutes. The DRY-FLO® starch is added and mixed thoroughly. Then the encapsulated fragrance is added and mixed thoroughly. The mixture is cooled to 50° C., poured into molds, and cooled to room temperature.

Example 10

Preparation of a Detergent

| Ingredient | Amount (g) |
| --- | --- |
| Sodium lauryl sulfate | 15 |
| Sodium lauryl ether sulphate | 10 |
| Magnesium aluminum silicate | 30 |
| Sodium Carbonate | 19.5 |
| Sodium disilicate | 2 |
| Sodium Perborate | 15 |
| Sodium polycarboxylate (acrylic/maleic) | 3 |
| Polyester terephthalate | 2 |
| Protease enzyme | 0.5 |
| Encapsulated fragrance | 0.75 |
| Optical brightener | 0.2 |
| Sodium phosphonate | 1.55 |
| TAED bleach activator | 0.5 |

The fragrance is encapsulated using the starch of Example 2 and the method of Example 3 in which the fragrance is substituted for the orange oil. The ingredients are blended together.

Example 11

Preparation of a Phosphate-Free Detergent

| Ingredient | Amount (g) |
| --- | --- |
| Magnesium Aluminum Silicate | 30 |
| Sodium Percarbonate | 15 |
| Sodium Alkyl Sulphate | 15 |
| Sodium Alcohol Ethoxylate | 10 |
| Dimethylamine Oxide | 6.75 |
| Sodium Carbonate | 15 |
| Sodium Sulphate | 7 |
| Encapsulated Fragrance | 1.25 |

The fragrance is encapsulated using the starch of Example 2 and the method of Example 3 in which the fragrance is substituted for the orange oil. The ingredients are blended together.

Example 12

Preparation of an Orange Oil Emulsion

| Ingredient | Amount (g) |
| --- | --- |
| Orange oil (one fold) | 5.8 |
| Orange oil (five fold) | 1.4 |
| Ester gum | 4.8 |
| Starch | 12 |
| Sodium benzoate | 0.15 |
| Citric acid | 0.30 |
| Water | 75.55 |

The starch used was that of example 2 except that the hydrolysis was allowed to proceed to a DE of 26 and a viscosity of 28 sec at 25% solids and 22° C. using the funnel method.

The ester gum was thoroughly dissolved in the mixture of the orange oils at room temperature using constant agitation. The sodium benzoate was then dissolved in the water after which the citric acid was dissolved in the solution. The starch was then dispersed in the solution using moderate agitation. The orange oil/ester gum was then added slowly with moderate agitation and the mixture was homogenized at 3000 psi and then at 5000 psi. The resultant emulsion has a viscosity of 75 cps using a Brookfied Viscometer with a #2 spindle at 60 rpm, a pH of 3.46, a median particle size of 0.265 microns and a mean particle size of 0.276.

Example 13

Preparation of a Beverage Using the Emulsion

| Ingredient | Amount (g) |
| --- | --- |
| Sugar | 11 |
| Emulsion of Example 12 | 0.015 |
| Sodium benzoate | 0.05 |
| Citric Acid | 0.2 |
| Yellow #5 | 0.004 |
| Yellow #6 | 0.004 |
| Water | 88.73 |

The sodium benzoate was dissolved in water. The citric acid, color, and sugar were then added. The emulsified orange oil was then added. There was no ringing upon storage of the beverage.

We claim:

1. A modified starch comprising a starch derivative containing a hydrophobic group or both a hydrophobic and a hydrophilic group, said starch being degraded by glucoamylase capable of hydrolyzing both 1,4- and 1,6-alpha-D-glucosidic linkages of the starch.

2. The starch of claim 1, wherein the starch is degraded to a dextrose equivalent of from about 20 and up to about 80.

3. The starch of claim 2, wherein the starch is degraded to a dextrose equivalent of from about 30 to about 50.

4. The starch of claim 1, wherein the starch is selected from the group consisting of corn, waxy maize, tapioca, potato, and rice.

5. The starch of claim 1, wherein the starch has a viscosity of less than about 30 seconds as measured by the funnel method.

6. The starch of claim 5, wherein the starch has a viscosity of from about 8 to about 25 seconds.

7. The starch of claim 6, wherein the starch has a viscosity of from about 8 to about 15 seconds.

8. The starch of claim 1, wherein the starch derivative is gelatinized and the hydrophobic group comprises an alkyl or an alkenyl group which contains at least five carbon atoms or an aralkyl or aralkenyl group which contains at least six carbon atoms.

9. The starch of claim 1, wherein the starch is gelatinized and has been derivatized by treatment with at least about 0.1% of octenyl succinic acid anhydride on a starch dry weight basis.

10. A modified starch which has improved oxidation resistance comprising a starch derivative containing a hydrophobic group or both a hydrophobic and a hydrophilic group, said starch being degraded by glucoamylase capable of hydrolyzing both 1,4- and 1,6-alpha-D-glucosidic bonds of the starch, wherein the starch has encapsulation properties characterized by at least 40% load capacity and low surface oil less than about 3%.

11. A method for preparing a modified starch comprising:
   a. derivitizing a starch such that it contains a hydrophobic group or a hydrophobic and a hydrophilic group; and
   b. degrading the starch using glucoamylase capable of hydrolyzing both 1,4- and 1,6-alpha-D-glucosidic linkages of the starch.

12. The method of claim 11, wherein the starch is degraded to a dextrose equivalent of from about 20 and up to about 80.

13. The method of claim 12, wherein the starch is degraded to a dextrose equivalent of from about 30 to about 40.

14. The method of claim 11, wherein the starch is selected from the group consisting of corn, waxy maize, tapioca, potato, and rice.

15. The method of claim 11, further comprising the step of gelatinizing the starch prior to degradation.

16. The method of claim 11, wherein the hydrophobic group comprises an alkyl or an alkenyl group which contains at least five carbon atoms or an aralkyl or aralkenyl group which contains at least six carbon atoms.

17. The method of claim 11, wherein the derivatization is carried out using at least about 0.1% of octenyl succinic acid anhydride on a starch dry weight basis.

18. A method for preparing a modified starch which has improved oxidation resistance comprising:
   a. derivitizing a starch such that it contains a hydrophobic group or a hydrophobic and a hydrophilic group; and
   b. degrading the starch using glucoamylase capable of hydrolyzing both 1,4- and 1,6-alpha-D-glucosidic bonds of the starch, wherein the modified starch has encapsulating properties characterized by at least 40% load capacity an low surface oil less than about 3%.

19. An encapsulating agent comprising a modified starch comprising a starch derivative containing a hydrophobic group or both a hydrophobic and a hydrophilic group, said starch being degraded by glucoamylase capable of hydrolyzing both 1,4- and 1,6-alpha-D-glucosidic bonds of the starch.

20. An emulsifying agent comprising the starch of claim 1.

21. A method of encapsulating an active agent comprising the encapsulating agent of claim 9, the method comprising:
   a) forming a solution of the encapsulating agent; and
   b) emulsifying the active agent in the solution.

22. The method of claim 21, further comprising drying the emulsion to remove the water therefrom.

23. The method of claim 22, wherein the drying step is accomplished by spray drying.

24. A method of emulsifying an active agent comprising the emulsifying agent of claim 20, the method comprising:
   a) forming a solution of the encapsulating agent; and
   b) emulsifying the active agent in the solution.

25. A composition comprising the encapsulating agent of claim 19.

26. A composition comprising the emulsifying agent of claim 20.

27. An emulsion comprising the modified starch of claim 1.

* * * * *